US008439280B2

(12) United States Patent
Marchetti et al.

(10) Patent No.: US 8,439,280 B2
(45) Date of Patent: May 14, 2013

(54) NEBULIZING DEVICE FOR LIQUID SUBSTANCES

(75) Inventors: Fabio Marchetti, Povo (IT); Stefano Deflorian, Martignano (IT); Alessandro Faes, Martignano (IT); Gianluca Paolazzi, Giovo (IT)

(73) Assignee: Zobele Holding S.p.A., Trento (IT)

( * ) Notice: Subject to any disclaimer, the term of this patent is extended or adjusted under 35 U.S.C. 154(b) by 408 days.

(21) Appl. No.: 12/743,880

(22) PCT Filed: Nov. 20, 2007

(86) PCT No.: PCT/IT2007/000813
§ 371 (c)(1),
(2), (4) Date: Aug. 17, 2010

(87) PCT Pub. No.: WO2009/066329
PCT Pub. Date: May 28, 2009

(65) Prior Publication Data

US 2010/0308132 A1 Dec. 9, 2010

(51) Int. Cl.
*B05B 1/08* (2006.01)

(52) U.S. Cl.
USPC ....... 239/102.2; 239/44; 239/102.1; 239/326; 239/338

(58) Field of Classification Search ........... 239/44–51.5, 239/102.1, 102.2, 326, 338, 370; 128/200.14
See application file for complete search history.

(56) References Cited

U.S. PATENT DOCUMENTS 6,439,474 B2 * 8/2002 Denen ........................ 239/102.2
7,424,979 B1 * 9/2008 Chen .......................... 239/102.1
7,837,129 B2 * 11/2010 Schuerle et al. ........... 239/102.2
7,950,595 B2 * 5/2011 Feriani et al. .............. 239/102.2
2003/0066904 A1 * 4/2003 Hess et al. ................. 239/102.2
2006/0011739 A1 1/2006 Jaworski
2008/0217430 A1 * 9/2008 Feriani et al. .............. 239/102.2

FOREIGN PATENT DOCUMENTS

EP 0 897 755 2/1999
WO 03/068413 A1 8/2003
WO 03/099458 A2 12/2003
WO 2007/054920 A1 5/2007
WO 2007/120489 A1 10/2007

OTHER PUBLICATIONS

International Search Report, dated Aug. 6, 2008, from corresponding PCT application.

* cited by examiner

*Primary Examiner* — Jason Boeckmann
(74) *Attorney, Agent, or Firm* — Young & Thompson

(57) ABSTRACT

A nebulizing element for liquid substances for coupling to procurement elements, includes at least one membrane with a microperforated area; at least one piezoelectric element connected to an electronic circuit and coupled to the membrane to cause it to vibrate; at least one first and one second support that can be placed on top of one another and create, on their interior a compartment to contain the membrane, the piezoelectric element, and a space of limited dimension for the liquid to be nebulized, created beneath the membrane. The second support has an opening for the nebulized liquid outlet, located in correspondence with the perforated area of the membrane. The nebulizing element also includes at least one collector for the liquid that flows from the porous element to the collector itself by capillary action; at least one capillary opening to allow in the liquid to be nebulized and at least one outlet opening to aid air circulation.

16 Claims, 7 Drawing Sheets

FIG 9a
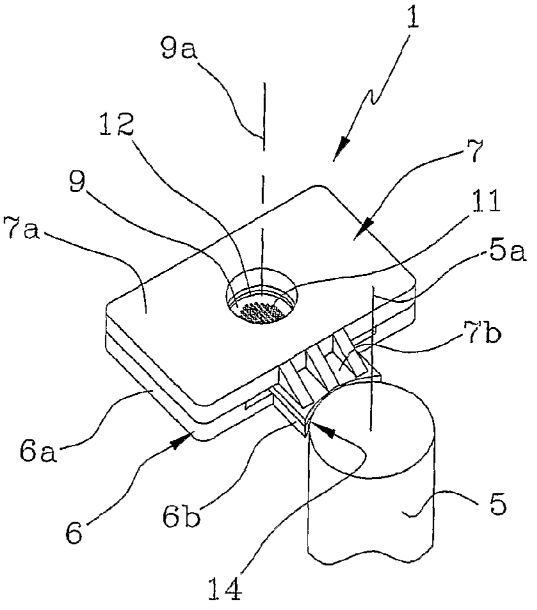
FIG 9b
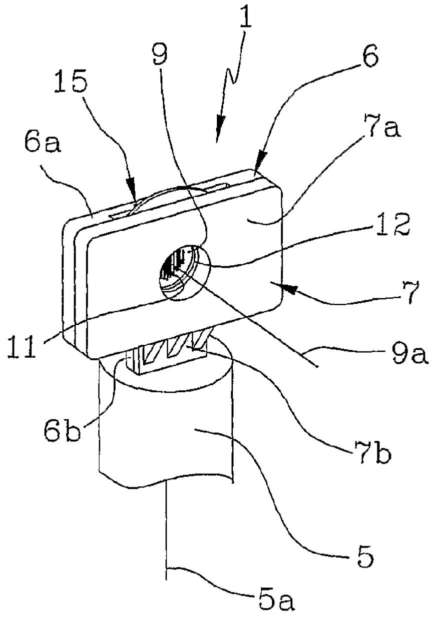
FIG 9c
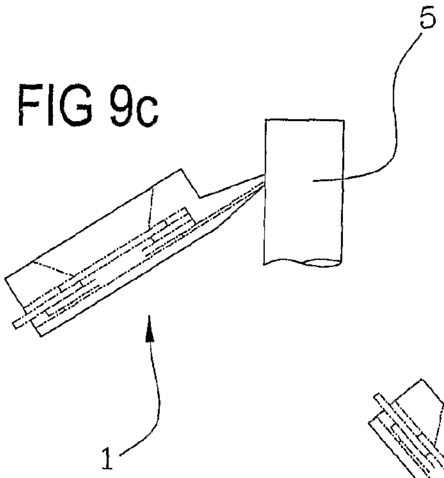
FIG 9d
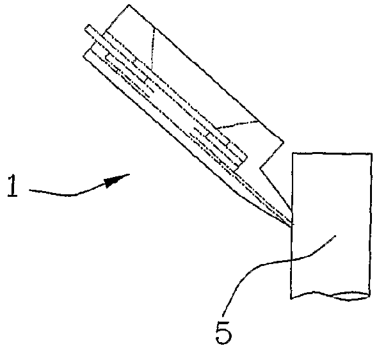
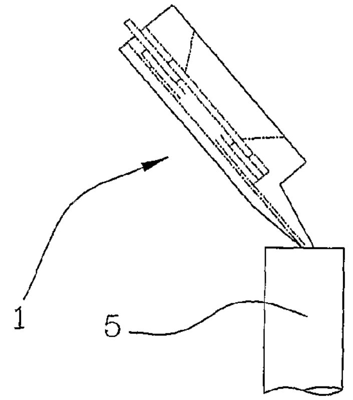
FIG 9e

NEBULIZING DEVICE FOR LIQUID SUBSTANCES

TECHNICAL FIELD

This invention concerns a nebulising device for liquid substances and an emanator device to dispense the liquids include said nebulising element.

STATE OF THE ART

The devices currently found on sale to diffuse perfumed fragrances, insecticides, medicines or aromatherapy oils into the environment preferably use emanation systems that issue ultrasounds.

Using such devices it is possible to issue a set amount of a nebulised product into the environment without altering its chemical composition and at a limited cost in terms of power.

These devices generally include a reservoir containing the substance to be nebulised, a porous element or wick, which is partly immersed inside the reservoir, and a nebulising element, to which the porous element conveys the liquid to be diffused. The nebulising element includes a microperforated membrane, which is made to vibrate at a suitable oscillation frequency by an associated piezoelectric element. The piezoelectric element is in turn connected to an electronic circuit which, when powered from an outside source, such as a battery for example, causes said piezoelectric element to change in terms of dimensions.

The membrane and the piezoelectric element must be perfectly coupled, for example, using suitable connectors or by integrating the piezoelectric element directly into the membrane so that the movement caused by dimensional variations of the piezoelectric material is totally transferred to the membrane. The presence of the piezoelectric element must in no way interfere with the oscillation of the membrane.

The oscillation of the membrane nebulises the liquid substance into the environment, without altering it chemically.

The membrane can also be connected to one or more oscillation sensors, beside the container, which regulate membrane oscillation frequency.

The effectiveness of ultrasonic nebulisation is linked to different factors such as, for example, the physical and chemical properties of the liquid, the type and size of the holes in the membrane and the membrane's oscillation frequency. This latter characteristic, which has a notable influence, not only depends on the characteristics of the membrane (material, thickness, etc. . . . ), but also on the damping elements around it, such as for example, supporting elements or elements connecting to the other parts of the device.

Even interference of the porous element with the nebulising element will change the distribution of the membrane masses and/or cause a shift in the system's resonance, preventing it from vibrating at optimum frequency or in any case, at a constant frequency that is little influenced by external factors which can be difficult to control, such as the length of the porous element, for example. If the system does not operate at its resonance frequency, the oscillation amplitude of the membrane will vary and this can lead to non-optimum or ineffective nebulisation.

In fact, once the maximum dimensions for the holes in the membrane have been established and therefore, the size of the liquid particles to be diffused, the greater the oscillation of the membrane, the more mechanical energy will be transferred to the liquid particles projected into the environment and the further the liquid will be nebulised.

Some devices have partially overcome the problems arising from interference between the porous element and the membrane, by placing the porous section so it is offset compared to the membrane axis. However, this solution has failed to solve the problem completely, above all on account of the difficulties encountered in coupling the nebulising and porous elements.

The direct consequence of this ineffective coupling is a reduced flexibility in the nebulisation system and a lack of nebulising efficiency.

Therefore, the Applicant has found that the solutions used in known techniques can be improved from both a structural viewpoint and in terms of operation, overall dimensions, flexibility and effective nebulisation.

PURPOSE OF THE INVENTION

The purpose of this invention is to supply an element to nebulise liquid substances, which is able to eliminate the problems described here above.

Specifically, the aim of this invention is to supply a nebulising element for liquid substances that is able to be coupled stably to the liquid procurement means, such as a porous element for example, without changing the vibration frequency of the whole nebulising system.

Moreover, it is the purpose of this invention to create a nebulising element for liquid substances that allows effective and constant liquid substance diffusion into the environment.

Lastly, the purpose of this invention is to create a nebulising element for liquid substances that is structurally simple, small in size and easily industrialised. It must also have limited costs and be easily adaptable to the various types of emanation devices.

According to this invention, a nebulising element for liquid substances is made with the characteristics present in one or more of the annexed claims.

BRIEF DESCRIPTION OF THE DRAWINGS

The invention will be described with reference to the annexed drawings, illustrating an embodiment example that is in no way limited, in which:

FIG. 9*a* shows a first configuration of the nebulising element illustrated in FIG. 3 coupled with a porous element;

FIG. 9*b* shows a second configuration of the nebulising element illustrated in FIG. 4 coupled with a porous element;

FIGS. 9*c*-9*e* show other coupling configurations between the nebulising element and the porous element;

DETAILED DESCRIPTION OF THE PREFERRED EMBODIMENTS OF THE INVENTION

Figure 1:
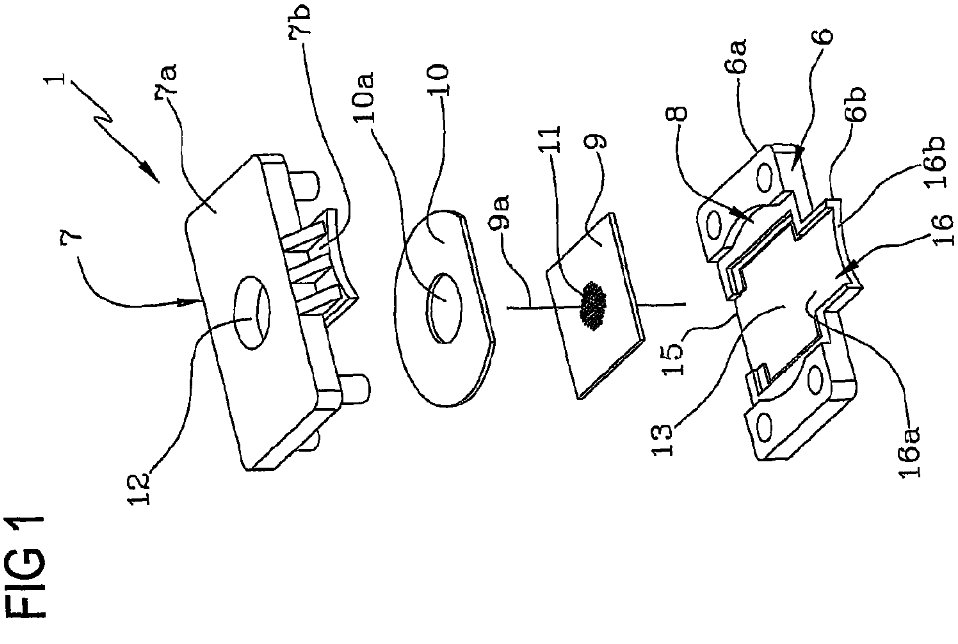
FIG. 1 shows an exploded view of an initial configuration of a nebulising element for liquid substances according to this invention.

With reference to the annexed figures, 1 has been used to indicate, overall, a nebulising element for liquid substances that is the subject of this invention.

Advantageously, the nebulising element 1 includes at least a first 6 and a second 7 support, which can be placed over one another and defining a container 8 on their interior.

Inside the container 8, the nebulising element 1 includes at least one membrane 9 coupled to a piezoelectric element 10, which is in turn connected to an electronic circuit 20.

This latter, which can be electrically connected to a power source, such as a battery 22 for example, causes the piezoelectric element 10 to change size. These controlled deformations within the piezoelectric element 10 cause the membrane 9 to vibrate. The special coupling between the membrane 9 and the piezoelectric element 10 causes the membrane 9 to vibrate along an axis 9*a* which is perpendicular to the surface on which the membrane 9 rests.

The electronic circuit 20 needs to guarantee a suitable pulse to the piezoelectric material in terms of intensity, duration, form and frequency, to foster the correct excitement of the material forming the piezoelectric element 10.

The nebulising element 1 can be coupled to a liquid procurement means 5, such as for example, a porous element impregnated with a liquid to be diffused, contained inside a reservoir 4.

For the sake of simplicity, when continuing with the description, reference will be made to a porous element 5 instead of a liquid procurement means. The porous element 5 is preferably to be made in fibre, glass fibre, porous plastic or in a similar material with a porousness somewhere between 30% and 80%, preferrably 50%.

The fluid is channelled between the nebulising element 1 and the porous element 5; in other words, the liquid from the porous element 5 flows into the nebulising element 1, via capillary action, until it reaches the proximity of the membrane 9.

Figure 2:
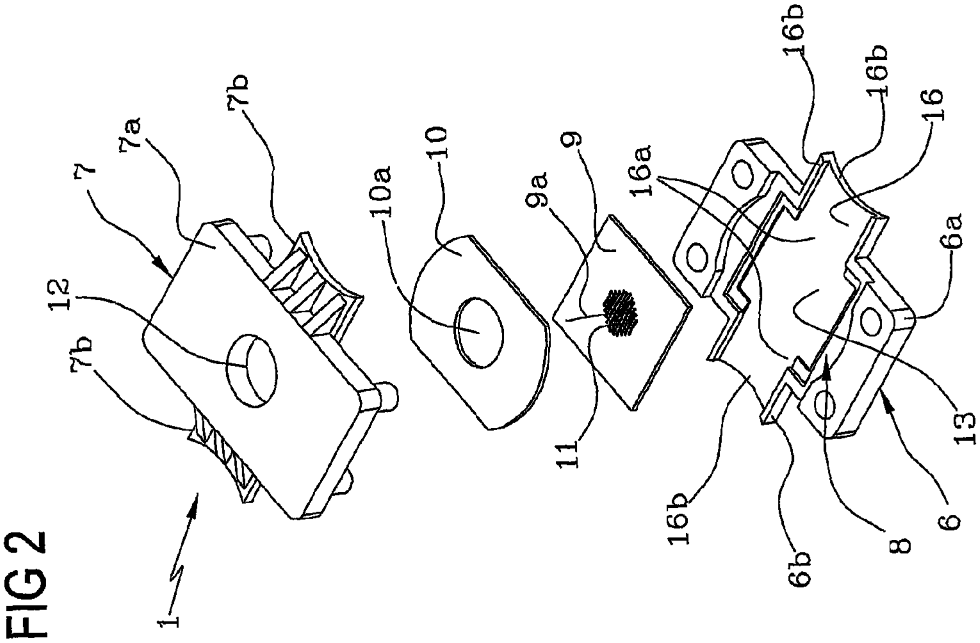
FIG. 2 shows an exploded view of a second configuration of a nebulising element for liquid substances according to this invention.

As can be clearly seen in FIGS. 1 and 2, the membrane 9 includes—preferably in a central position—at least one area 11 comprised of a number of small through holes.

These holes, which preferably have a round or square section, have a 30 maximum cross dimensions such as a side or diameter for example, preferably between 5 and 20 ●m, with a density, in the case of holes with a 10 ●m diameter, for example, of 50 holes per square millimeter. The membrane 9 is preferably made in metal, plastic or even better, in silicon, quartz or glass and may be of extremely reduced thickness, between 10 and 100 ●m—preferably between 30 and 70 ●m. In the case of a membrane 9 in silicon, it is best to make it by covering the outer surfaces of the membrane with a layer of silicon nitrides or silicon oxides with passivation action, or with a layered combination of these substances, followed by lithography and subsequent chemical attack (bath in a basic solution for anisotropic etching) or physical attack (deep reactive ion etching, reactive ion 10 etching) to make the holes in the membrane. Subsequent further chemical and physical attacks will make the fine substrate finer, until a membrane 9 of the required thickness is obtained.

Beneficially, the second support 7 presents an opening 12, preferably in a central position, which, when the nebulising element 1 is fully assembled, is placed level with the perforated area 11 of the membrane 9, so as to emit the nebulised liquid. This opening 12 may have parallel sides as illustrated in FIGS. 3-8, or reciprocally slanted sides, preferably flared as illustrated in the FIGS. 13*a* and 13*b*, to aid the emission of particles and prevent the condensation from forming.

The nebulising element 1 is therefore preferably made by placing the following onto one another in sequence: the first support 6; the membrane 9; the piezoelectric element 10 and the second support 7, as illustrated in the FIGS. 1 and 2.

To aid the assembly stage, the piezoelectric element 10 is suitably shaped, at least around the edges, as can be seen in FIGS. 1 and 2. It is preferable for the piezoelectric element 10 to have a ring shape with a hollow central section 10*a*, coupled by placing it over the perforated central area 11 of the membrane 9.

The piezoelectric element 10 is connected to the membrane 9 by special connecting elements; for example, the piezoelectric element 10 can be glued, 30 soldered or directly integrated to the membrane 9. The electronic circuit 20 is connected to the piezoelectric element 10 by electrical connections 23 which, for example, are directly soldered to the piezoelectric element 10 or connected electrically to it via mechanical interference obtained with the supports 6 and 7 respectively. Lastly, the membrane 9 and piezoelectric element 10 are enclosed between the two supports 6 and 7. Between the first support 6 and the membrane 9 there is a collector 13 to collect the liquid which, on account of capillary action flows from the porous element 5 to the collector 13 itself. More precisely, the collector 13 is created on the first support 6, and in particular, on its upper surface, which is delimited at the top by the membrane 9. The collector 13 is an area of limited size, created beneath the membrane 9, between the membrane 9 itself and the first support 6. It has a height of between 5 and 150 μm (preferably, between 20 and 100 μm) and lateral dimensions that can vary between 3 and 6 mm (preferably between 4 and 5 mm). What counts is that, in any case, the lateral dimensions of the collector 13 are less than or at most, equal to the lateral dimensions of the membrane 9.

Therefore, the dimensions of the liquid collector 13 are such that they allow the procurement of liquid inside the collector 13 exclusively by capillary action.

Figure 6:
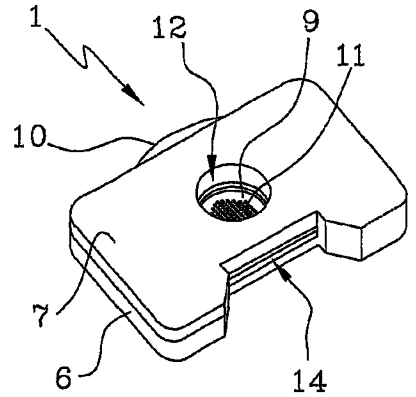
Figure 7:
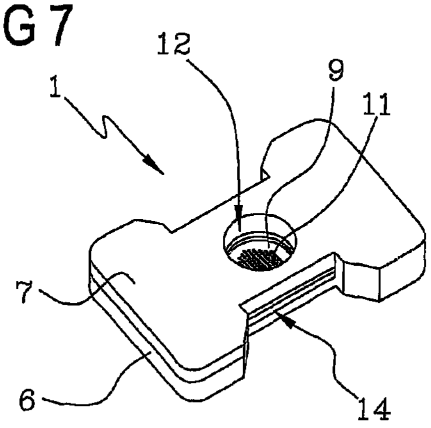
Figure 8:
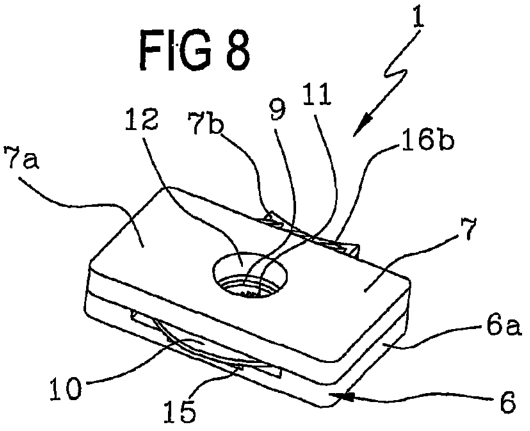
FIG. 8 shows a rear perspective view of the nebulising element that is the subject of this invention.

The nebulising element 1 includes at least one capillary opening 14, which can be seen in the FIGS. 3-7, to allow the liquid for nebulising to enter the collector 13; it also has at least one outlet opening 15, which can be seen in FIGS. 1, 2 and 8, to allow air circulation and discharge and to facilitate fluid movement through capillary action.

In an initial embodiment, illustrated in FIGS. 6 and 7, both the capillary opening 14 for incoming liquid and the air outlet opening 15 are situated so that they are at least level with a perimeter portion of the collector 13. This means that each one will preferably delimit at least one side of the collector 13. In these configurations, the porous element 5 takes up position against the capillary opening 14 that makes it easier for the liquid on the surface of the porous element 5 to enter directly into the collector 13.

Advantageously, the nebulising element 1, in the preferred configuration, as illustrated in the formats shown in FIGS. 3, 4, 5 and 8, includes a capillary channel 16 that branches from the collector 13 to place it in fluid communication with the porous element 5.

The capillary channel 16 includes a first end 16*a* communicating with the liquid collector 13, and a second end 16*b*, opposite to the first, which can be coupled to the porous element 5. In this configuration, the capillary opening 14 for liquid coming into the collector 13 of the nebulising element 1, is located level with the second end 16*b* of the capillary channel 16.

In this case too, the discharge opening 15 can be positioned level with a perimeter side of the collector 13, as shown in FIG. 8. The capillary opening for incoming liquid 14 and the air discharge outlet 15 can be located along the same axis—as shown in the annexed figures—or out of line with one another. It is preferable for the two openings 14 and 15 to remain coplanar, whether they are located along the same axis or out of line.

In an initial layout, the capillary channel 16, illustrated in FIGS. 1 and 2, is at least partially defined by the second support 7 and the first 6 support; specifically, in FIGS. 1 and 2 it can clearly be seen that the channel 16 is created in the top surface of the first support 6.

Figure 3:
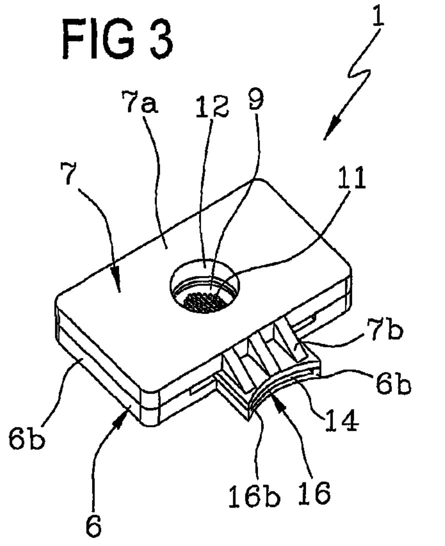
FIGS. 3-7 show different embodiment variations of the nebulising element illustrated in FIG. 1.
Figure 4:
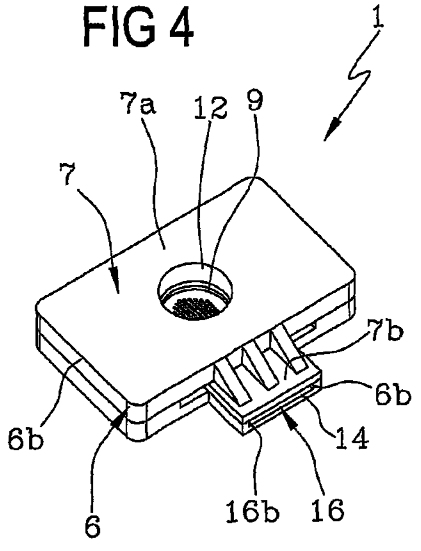

In particular, with reference to FIGS. 3, 4 and 8, the first 6 and second 7 supports are each comprised of a main body 6*a*, 7*a*, which is polygonal or circular in shape, and at least one respective appendage 6*b*, 7*b* projecting from its main body 6*a*, 7*a*, and with which it is coplanar.

The capillary channel 16 is defined by the coupled appendages 6*b*, 7*b* of the first 6 and second 7 support.

Figure 5:
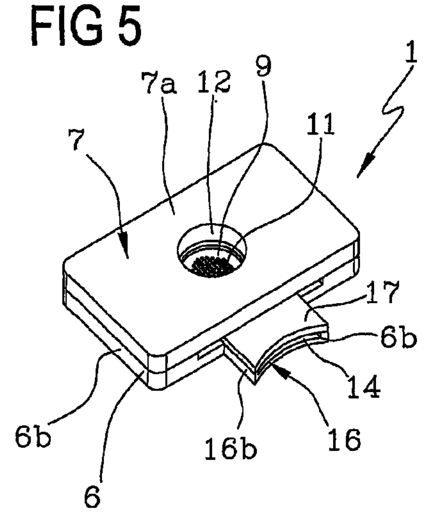

Alternatively, as shown in FIG. 5, only the first support 6 has an appendage 6*a* and therefore, in this case the capillary channel 16 is at least partially defined by the first support 6 and by at least one covering plate 17, preferably in metal.

To allow the liquid to travel through the capillary channel 16 and therefore, inside the collector 13, the capillary channel 16 and in particular, its second end 16*b*, is in extremely close contact with the porous element 5. In other words, the second end 16*b* of the capillary channel 16 is at least partially resting against a coupling surface of the porous element 5.

Depending to the shape of the coupling surfaces on the porous element 5, the second end 16*b* of the capillary channel 16, or the capillary opening 14 for incoming liquid is shaped to adapt to said form.

As shown in the annexed Figures, the capillary channel may be in different shapes, for example, trapezoidal (FIG. 14) or rectangular (FIG. 4). The second end 16*b* of the capillary channel 16 may be formed differently: for example, it may be arched (FIGS. 3 and 5), to follow the side surface of the cylindrical porous element 5 better; or straight (FIGS. 4 and 14), for use with porous elements with coupling surfaces that are curved or straight. To make sure that liquid flows into the collector 13 by capillary action, at least one part of the capillary opening 14 must be in intimate contact with the surface of the porous element 5.

In the case where there is no capillary channel 16 (FIGS. 6 and 7) too, the capillary opening 14 may have a straight or curved profile.

At least one part of the second end 16*b* of the capillary channel 16, and therefore, at least one part of the capillary opening 14, needs to rest upon and exert a slight pressure against the porous element 5, to facilitate liquid input into the channel 16 by means of capillary action.

Figure 14:
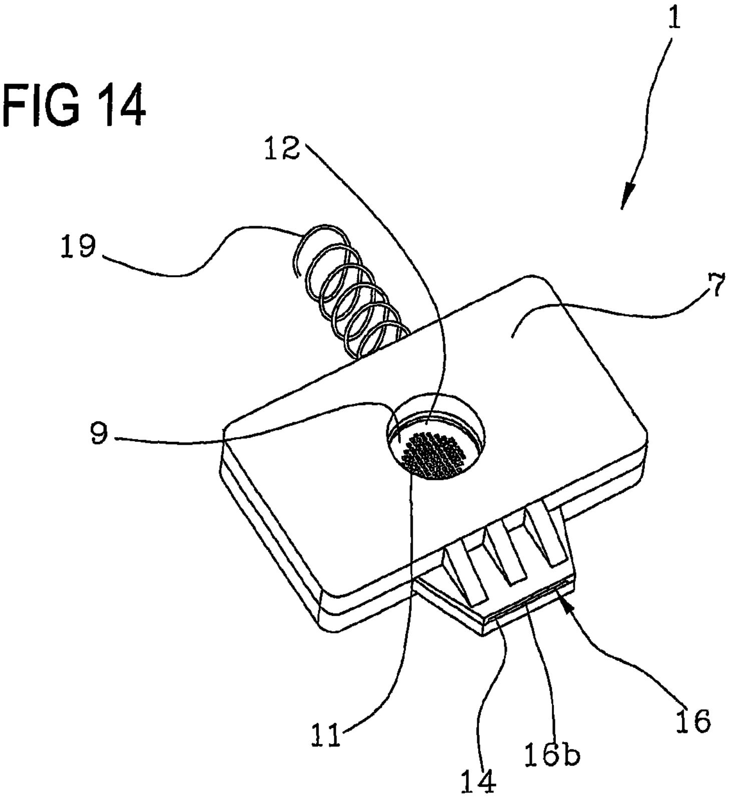
FIG. 14 shows another embodiment of the nebulising element, associated with an elastic element.

To this end, the nebulising element 1 is beneficially coupled to elastic bodies 19—schematically illustrated in FIG. 14—comprised, for example, of elastic frames or pressure springs. These elastic bodies 19 will keep the nebulising element 1 in position against the porous element 5, guaranteeing constant contact between the capillary opening 14 and the coupling surface of the porous element 5 over time. The relevant position of the nebulising element 1 compared to the porous element 5 can be changed as required. FIGS. 9*a*-9*e* show coupling configuration examples. The nebulising element 1 can be placed vertically, as illustrated in FIG. 9*b*, and associated to the top surface of the porous element 5, or it can be placed horizontally, as illustrated in FIG. 9*a*, and associated to the side surface of the porous element 5. In this latter configuration, the nebulising element 1 forms a right angle with the axis 5*a* of the porous element 5. Other configurations have the nebulising element 1 so that it is angled compared to the axis 5*a* of the porous element 5, so as to form an acute angle (FIGS. 9*d* and 9*e*) or an obtuse angle (FIG. 9*c*).

Figure 13A:
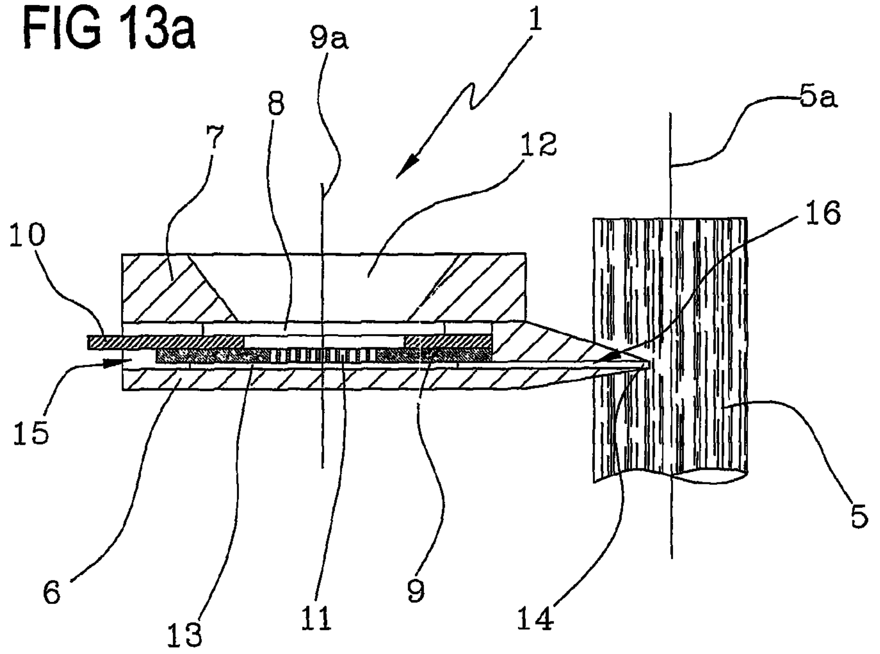
FIGS. 13*a* and 13*b* each show a partially sectioned side view of another two alternative embodiments of the nebulising element that is the subject of this invention.
Figure 13B:
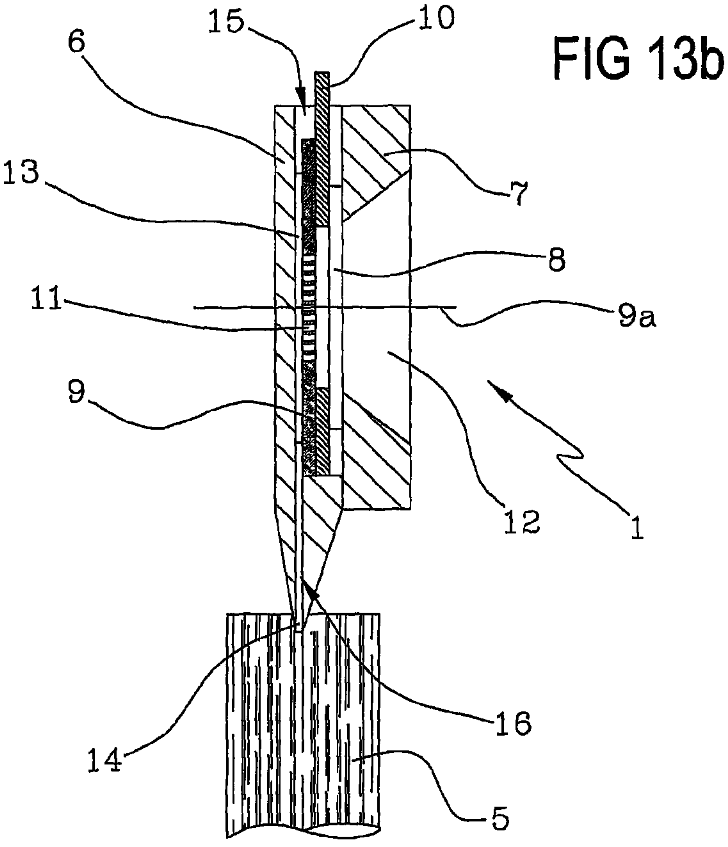

Two more alternative configurations are illustrated in the FIGS. 13*a* and 13*b*: in both, the second end 16*b* of the capillary channel 16 is inserted inside the porous element 5. To create this type of coupling, the second end 16*b* of the capillary channel 16 will preferably be pointed.

For these latter two configurations, it may not be necessary to use the pressure elastic bodies 19 described previously.

The dimensions of the nebulising element 1 are quite limited, with total side dimensions varying preferably between 6 and 15 mm, both in terms of length and width, and a total height that will preferably be within the range of 2-3 mm. The capillary channel 16 has a variable length, preferably between 2 and 4 mm, while the membrane 9 has lateral dimensions between 4 and 6 mm.

The capillary channel 16 needs to have a cross dimension that is less than the cross dimension of the membrane 9.

The central perforated area 11 of the membrane 9 will preferably have a diameter that can vary from between 1 and 4 mm.

Given the reduced dimensions, the best material to be used—at least for creating the first support 6—is quartz, which allows for extremely precise operations. Alternatively, it is possible to use crystal material, amorphous material, metal or plastic. The supports can be created using the MEMS technique, mechanically, or using moulding processes. The various processing operations will affect the tolerance that can be obtained on the item.

In any case, if the material used has a low degree of wetting tension and therefore, it can slow down the capillary action movement of the liquid, the surfaces of the supports and in particular, the one coming into contact with the liquid, should be treated to obtain sufficient wetting tension.

Figure 10:
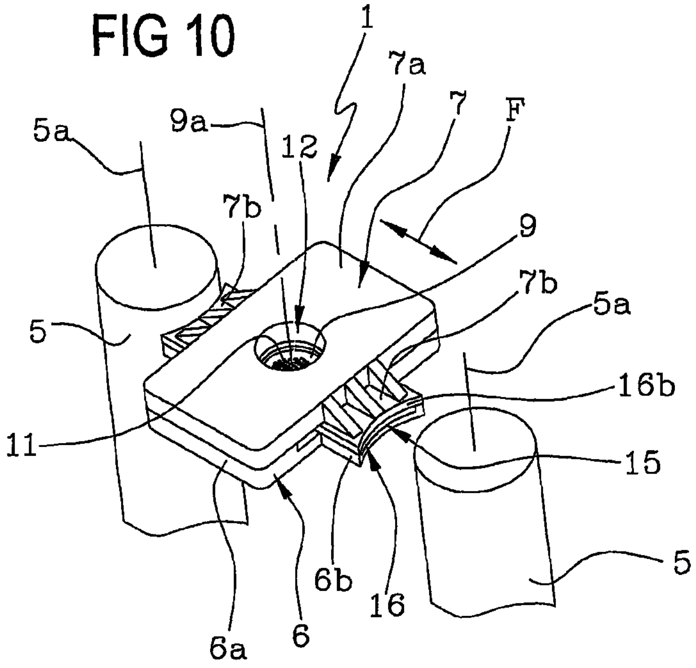
FIG. 10 shows the nebulising element illustrated in FIG. 2 that can be coupled with two different porous elements.

Alternative configurations are shown in FIGS. 2, 7 and 10. These configurations require the nebulising element 1 to be symmetrical and able to be coupled selectively with several porous elements 5. In the configurations shown in FIGS. 2 and 10, the nebulising element 1 has at least two capillary channels 16, while in the configuration shown in FIG. 7, the nebulising element 1 has no capillary channels 16. In the configuration illustrated in FIGS. 2 and 10, the channels 16 are located symmetrically compared to the collector 13. Alternative solutions may also include more than two channels 16, preferably set out on the same level and not necessary aligned with or symmetrical to the collector 13.

Each capillary channel 16 is activated individually, so as to be able to place the collector 13 in fluid communication with a single porous element 5 at a time. The capillary channel 16 is activated by physically moving the nebulising element 1 along a direction F, limited to within the support surface of the nebulising element 1 itself. The process is the same for the nebulising element 1 according to the configuration in FIG. 7.

Each porous element 5 is partially immersed inside a respective reservoir 4, with each reservoir containing a liquid with different characteristics, such as different fragrances.

For nebulising elements 1 that can be coupled to more than one porous element 5, the capillary opening 14 for incoming liquid is level with the second end 16*b* of the enabled capillary channel 16 from time to time, while the air outlet opening 15 is level with one or more of the second ends 16*b* of the capillary channels 16 that have not been activated.

In this way, whatever the geometry of the nebulising element, and as well as an opening for incoming liquid and an opening to issue nebulised liquid, there is always an air outlet opening that also aids air circulation inside the collector 13.

The nebulising element 1 that is the subject of this invention can be connected to an emanator device 2 for liquid substances.

Figure 11:
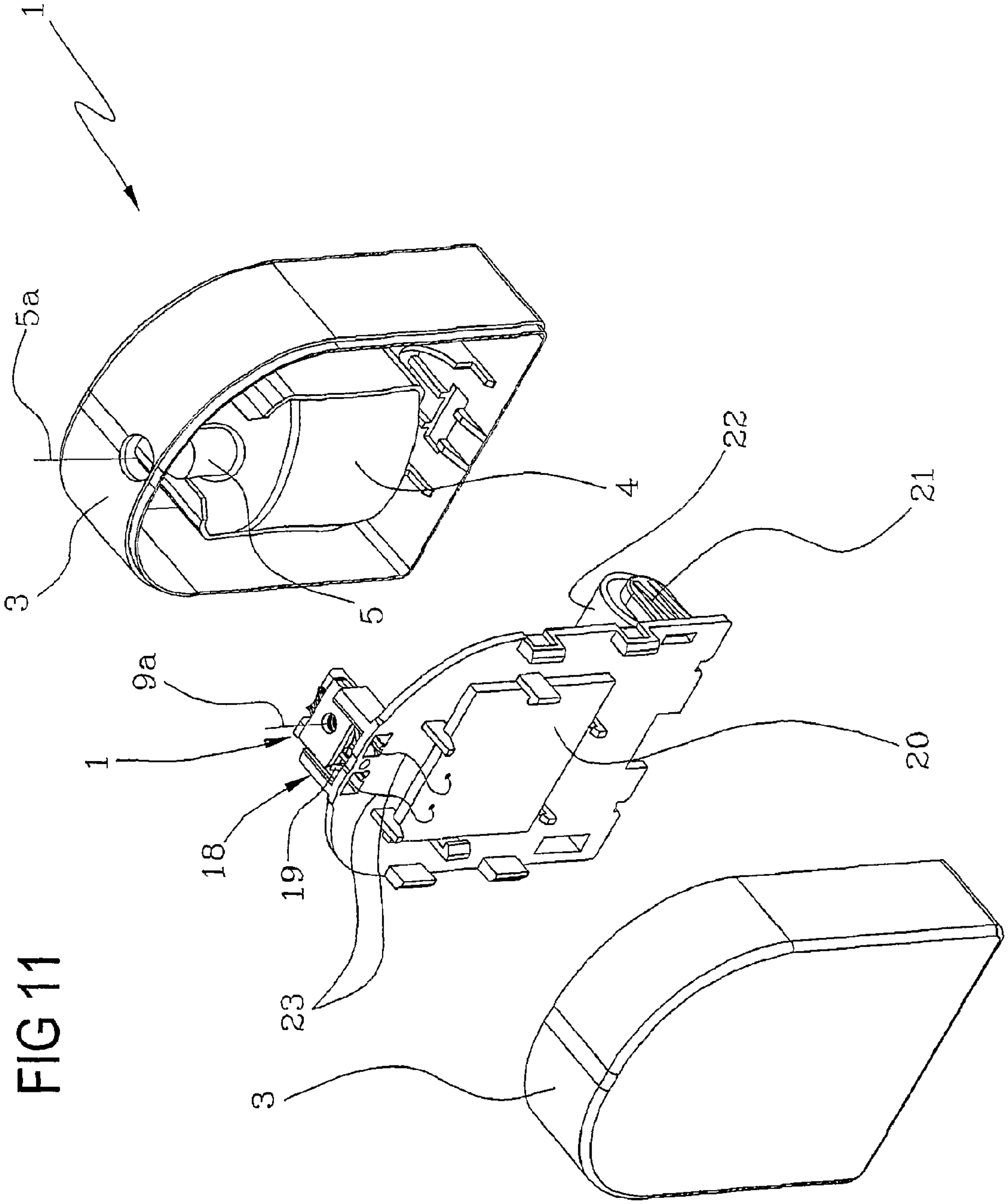
FIG. 11 shows a perspective view (exploded) of a first embodiment of a device to emanate liquid substances, including the nebulising element that is the subject of this invention.
Figure 12:
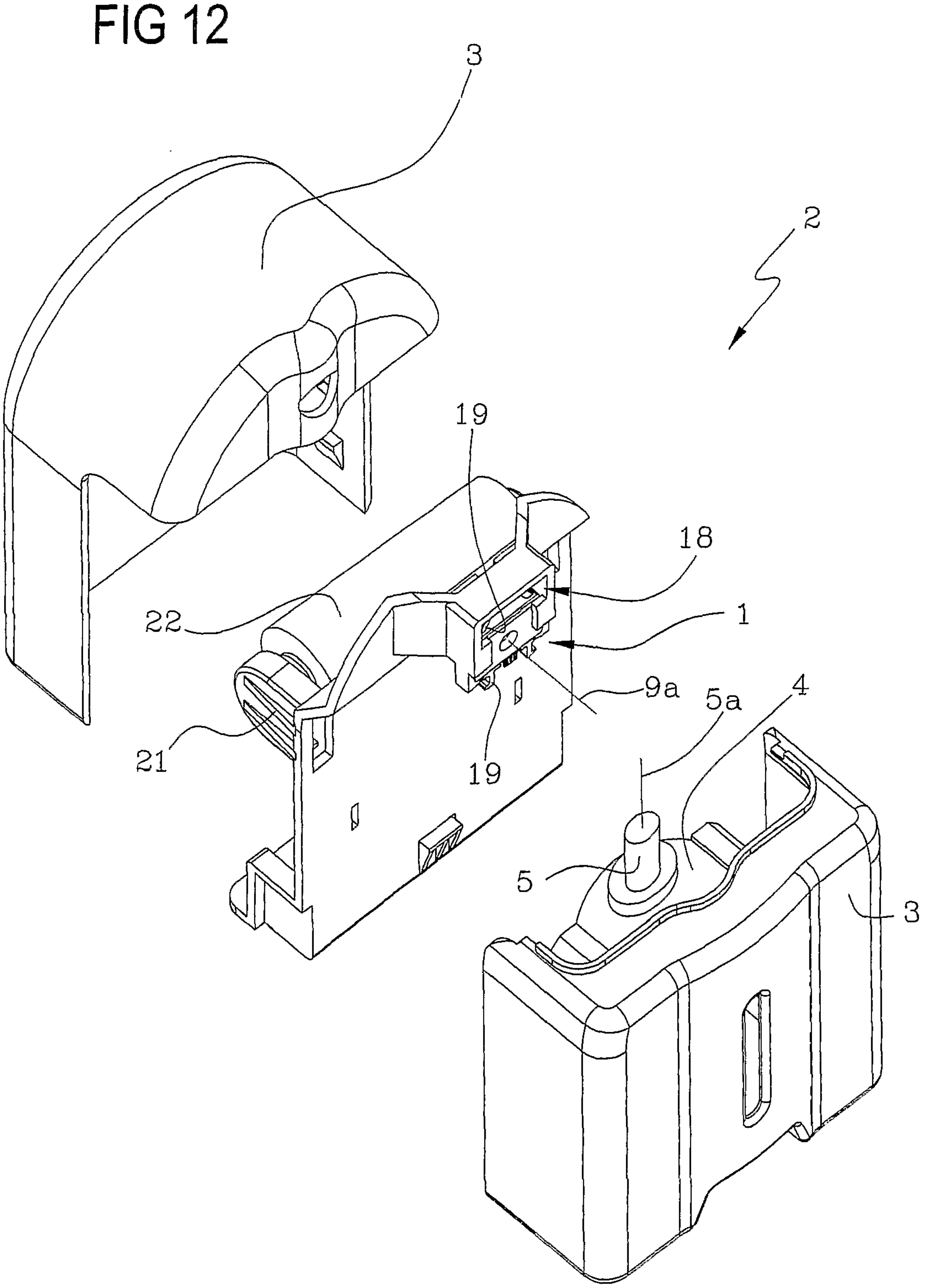
FIG. 12 shows a perspective view (exploded) of a second embodiment of a device to dispense liquid substances, including the nebulising element that is the subject of this invention.

As illustrated in FIGS. 11 and 12, the emanator device 2 includes at least one box container 3, at least one reservoir 4 to hold the liquid to be diffused and inside which a porous element 5 is partly immersed, a source of electric power, such as a battery 22 for example, suitably secured to the plastic part with special supports 21, and the nebulising element 1 that is the subject of this invention.

The nebulising element 1 is preferably housed inside seating 18 that has been placed vertically or horizontally to the axis 5*a* of the porous element 5. In other words, the seating 18 is positioned in such a way as to allow the nebulising element 1 to rest on a surface that is parallel or perpendicular to the development axis 5*a* of the porous element 5 to which it is coupled.

FIG. 11 shows an initial configuration for the emanator device 2 that is the subject of this invention, where the nebulising element 1 is set on a surface that is perpendicular to the axis 5*a* of the porous element 5. In this configuration, the vibration axis 9*a* of the membrane 9 is parallel to the axis of the porous element 5. The capillary channel 13 interferes with the side surface of the porous element 5. In this way, the oscillation of the membrane 9 is in no way constrained by the presence of the porous element 5, since the vibration plane of the membrane 9 is different from the coupling surface between the capillary channel 16 and the porous element 5, and more specifically, it is perpendicular.

FIG. 12 shows a second configuration for the emanator device 2 that is the subject of this invention, where the nebulising element 1 is set out on a surface parallel to the axis 5*a* of the porous element 5. In this configuration, the vibration axis 9*a* of the membrane 9 is perpendicular to the axis of the porous element 5. The capillary channel 13 interferes with the upper surface of the porous element 5, so as not to obstruct the vibration of the membrane 9, even in this case.

In this case too, the vibration plane of the membrane 9 is different from the coupling surface between the capillary channel 16 and the porous element 5, and more specifically, it is perpendicular.

Advantageously, the seating 18 contains the aforementioned elastic bodies 19 that keep the nebulising element 1 in constant contact with the porous element 5.

The elastic bodies 19 increase the disengagement between the nebulising element 1 and the device 2, so as to insulate it better against any outside disturbance that could interfere with the oscillation of the membrane 9, shifting vibration frequency and therefore preventing efficient nebulisation.

The emanator devices 2 fitting the nebulising element 1 set on a surface that is perpendicular to the axis 5*a* of the porous element 5 (as per the first configuration described here above and illustrated in FIG. 11) can be changed to emanator devices with multiple refills.

For multiple-refill devices, the nebulising element 1 with two or more capillary channels 16 or several capillary openings 14, is selectively moved along the direction F shown in FIG. 10 to couple with the porous element 5, which is soaked in the required substance.

Whichever configuration is used for the emanator device 2, the opening 12 of the second support 7 will always face outwards.

Due to capillary action, the liquid flows from the porous element 5 to inside the collector 13, where a liquid collection basin is created. When the device 2 is enabled, the piezoelectric element vibrates and causes the membrane 9 to vibrate. During its oscillation, the membrane 9 is wetted by the liquid in the collector 13. Capillary action causes the liquid to rise up through the holes in the membrane 9 and the single drops that form are launched and nebulised to the outside, through the opening 12 in the second support 7.

One of the functions of the capillary channel 16 is as a childproof safety system. In fact, the presence of the capillary channel 16 keeps the porous element 5 away from the nebulising area and therefore, from the opening 12 of the second support 7, which has to be visible and exposed to allow the substance to be diffused. With the channel 16, the reservoir 4 and the porous element 5 can be concealed inside the device 2, in a totally closed position that cannot be accessed by children, so as to prevent any of the liquid to be diffused from being accidentally swallowed.

The nebulising element that is the subject of this invention presents significant advantages.

The coupling between the nebulising element and the porous element is stable and will not change the vibration frequency of the membrane.

The offset layout between the membrane and the porous element in no way invalidates the functional operation of the nebulising element; it allows the membrane to vibrate at an operating frequency that aids a nebulisation which is both effective and constant over time, without the need to perform a frequency sweep through the electronic circuit 20. In this way, the device is able to operate at a single oscillating frequency.

The position of the porous element, which is offset compared to the membrane's vibration axis, means that the characteristic operating frequency of the membrane is only defined by the configuration of the nebulising element structure and not by the characteristics for coupling the membrane and the porous element, which are not easily defined.

The liquid flows along the channel and then reaches the collector exclusively due to capillary action, thanks to the particularly limited dimensions of the nebulising element and to the presence of an air outlet opening.

In fact, this latter allows air to circulate inside the chamber, facilitating the liquid's movement by capillary action as well as its natural diffusion within the surrounding environment. The presence of an air outlet opening that is separate from the opening through which the liquid is nebulised into the environment, means it is possible to reduce the power needed to nebulise the liquid into the environment.

The nebulising element conceived in this manner is a highly flexible system since it can be coupled to the porous element at different angles, making it possible to use different forms of nebulising device inside which the nebulising element that is the subject of this invention can be inserted.

The nebulising element that is the subject of this invention is simple in structural terms, small, easy to industrialise and cheap to produce.

The invention claimed is:

1. A nebulizing element for liquid substances that can be coupled to a porous element for a liquid, the nebulizing element comprising:

at least one membrane with a microperforated area;

at least one piezoelectric element electrically connected to an electronic circuit powered electrically, the piezoelectric element being coupled with the membrane to cause the membrane to vibrate along an axis that is perpendicular to the position of the membrane;

at least one first and one second support that can be placed over one another to define, on an interior thereof, a compartment to contain the membrane and the piezoelectric element, the second support defining an opening therethrough through which to emit the nebulised liquid; and at least one collector for collecting the liquid that, due to capillary action, flows from the porous element to the collector, the collector being positioned between the first support and the membrane, the collector comprising at least one capillary opening for receiving the incoming liquid into the collector to be nebulised, at least a portion of the capillary opening resting upon the porous element, and at least one outlet opening, separate from the second support opening through which the liquid is nebulized into the environment, to allow air circulation inside the collector.

2. The nebulizing element according to claim 1, further comprising: placing the first support, the membrane including the microperforated area, the piezoelectric element, and the second support with an opening corresponding to the perforated area of the membrane, one on top of the other in sequence.

3. The nebulizing element according to claim 1, wherein the collector is created on the first support and is defined by the first support and by the perforated membrane.

4. The nebulizing element according to claim 1, further comprising at least one capillary channel placing the collector and the porous element in fluid communication with one another.

5. The nebulizing element according to claim 4, wherein the capillary channel includes a first end communicating with the liquid collector and a second end, opposite to the first end, that can be coupled with the porous element.

6. The nebulizing element according to claim 5, wherein the capillary opening for incoming liquid coincides with the second end of the capillary channel.

7. The nebulizing element according to claim 4, wherein the capillary channel is at least partially defined by the first support and by the second support.

8. The nebulizing element according to claim 4, wherein the capillary channel is at least partially defined by the first support and by at least one cover plate.

9. The nebulizing element according to claim 5, wherein the capillary channel interferes with the porous element to aid the entry of liquid into the collector through capillary action.

10. The nebulizing element according to claim 9, wherein the second end of the capillary channel rests against a coupling surface of the porous element, the second end being countershaped to the coupling surface of the porous element.

11. The nebulizing element according to claim 9, wherein the second end of the capillary channel is pointed and penetrates the porous element.

12. The nebulizing element according to claim 5, further comprising at least two capillary channels that can be selectively coupled with a respective porous element, each capillary channel, when selectively enabled, places the connector in fluid communication with the porous element impregnated with the liquid to be nebulized.

13. The nebulizing element according to the claim 12, wherein, when one of the two capillary channels is selectively enabled, the outlet opening to aid air circulation coincides with the second end of at least one deactivated capillary channel.

14. The nebulizing element according to claim 1, wherein the nebulizing element is configured to be coupled with the porous element in such a way that the vibration axis of the membrane will be parallel to the axis of the porous element.

15. The nebulizing element according to claim 1, wherein the nebulizing element can be coupled with the porous element in such a way that the vibration axis of the membrane is perpendicular to the axis of the porous element.

16. The nebulizing element according to claim 1, wherein the height of the collector is between 5 and 150 μm.

* * * * *

UNITED STATES PATENT AND TRADEMARK OFFICE

CERTIFICATE OF CORRECTION

PATENT NO. : 8,439,280 B2
APPLICATION NO. : 12/743880
DATED : May 14, 2013
INVENTOR(S) : Marchetti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 497 days.

Signed and Sealed this
Eighth Day of September, 2015

Michelle K. Lee
*Director of the United States Patent and Trademark Office*